(12) United States Patent
Lyons et al.

(10) Patent No.: US 8,187,301 B2
(45) Date of Patent: May 29, 2012

(54) SUTURE LOCK

(75) Inventors: David F. Lyons, Palo Alto, CA (US);
Peter M. Breining, San Mateo, CA (US)

(73) Assignee: Anpa Medical, Inc., San Mateo, CA (US)

( * ) Notice: Subject to any disclaimer, the term of this patent is extended or adjusted under 35 U.S.C. 154(b) by 19 days.

(21) Appl. No.: 12/983,753

(22) Filed: Jan. 3, 2011

(65) Prior Publication Data

US 2011/0098743 A1    Apr. 28, 2011

Related U.S. Application Data

(63) Continuation of application No. 10/841,255, filed on May 7, 2004, now Pat. No. 7,862,584.

(60) Provisional application No. 60/468,496, filed on May 7, 2003.

(51) Int. Cl.
*A61B 17/04*    (2006.01)

(52) U.S. Cl. ....................................................... 606/232

(58) Field of Classification Search .................. 606/232, 606/300; 24/115 R, 129 R, 130, 339; 289/13, 289/14
See application file for complete search history.

(56) References Cited

U.S. PATENT DOCUMENTS 3,228,640 A * 1/1966 Wolsh .............................. 24/339

\* cited by examiner

*Primary Examiner* — Julian Woo
(74) *Attorney, Agent, or Firm* — Ryan Kromholz & Manion, S.C.

(57) ABSTRACT

A suture lock to be used with a suture thread. The suture lock comprises at least one passageway for receiving a suture thread, with the passageway having at least a portion of its length having a longitudinal side opening arranged to slidably receive the suture. The passageway is tapered inwardly and including an interior surface having inwardly converging teeth. The invention may also comprise a suture lock having an adjustable channel located within the suture lock. The channel may be adjusted between an open and a closed position, thereby allowing the suture to be secured. Translation of the suture itself may be utilized to adjust the positioning of the channel. The suture lock may contain a releasable device to retain the channel in multiple positions between the closed and open position.

1 Claim, 10 Drawing Sheets

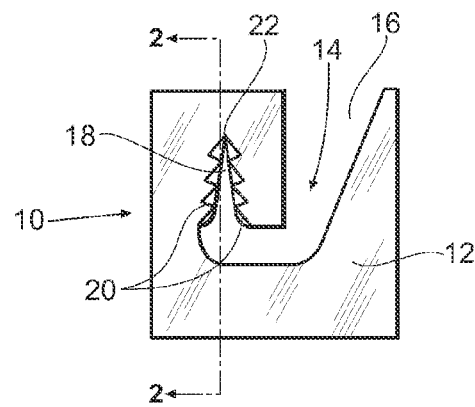
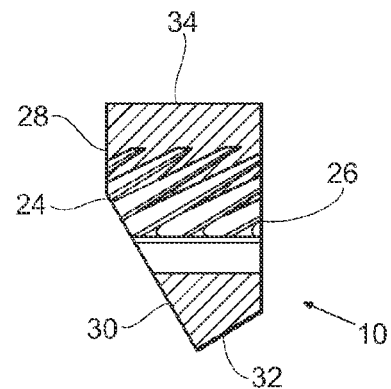
Fig. 1　　　　Fig. 2
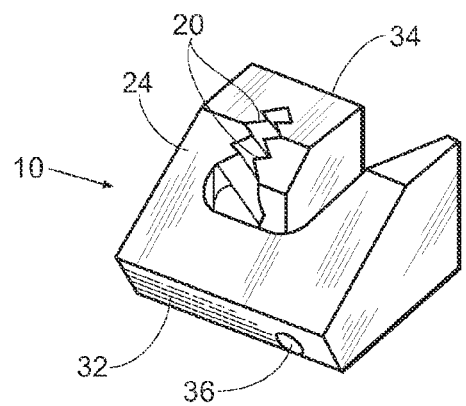
Fig. 3
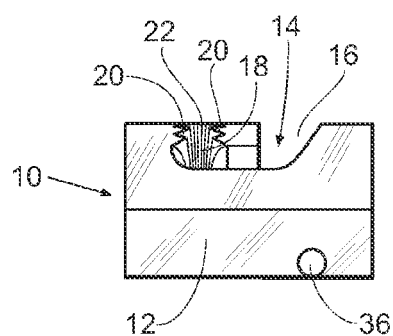
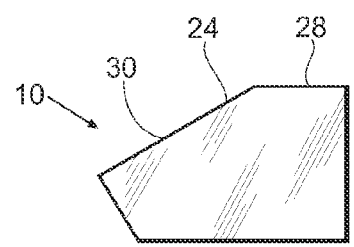
Fig. 4　　　　Fig. 5

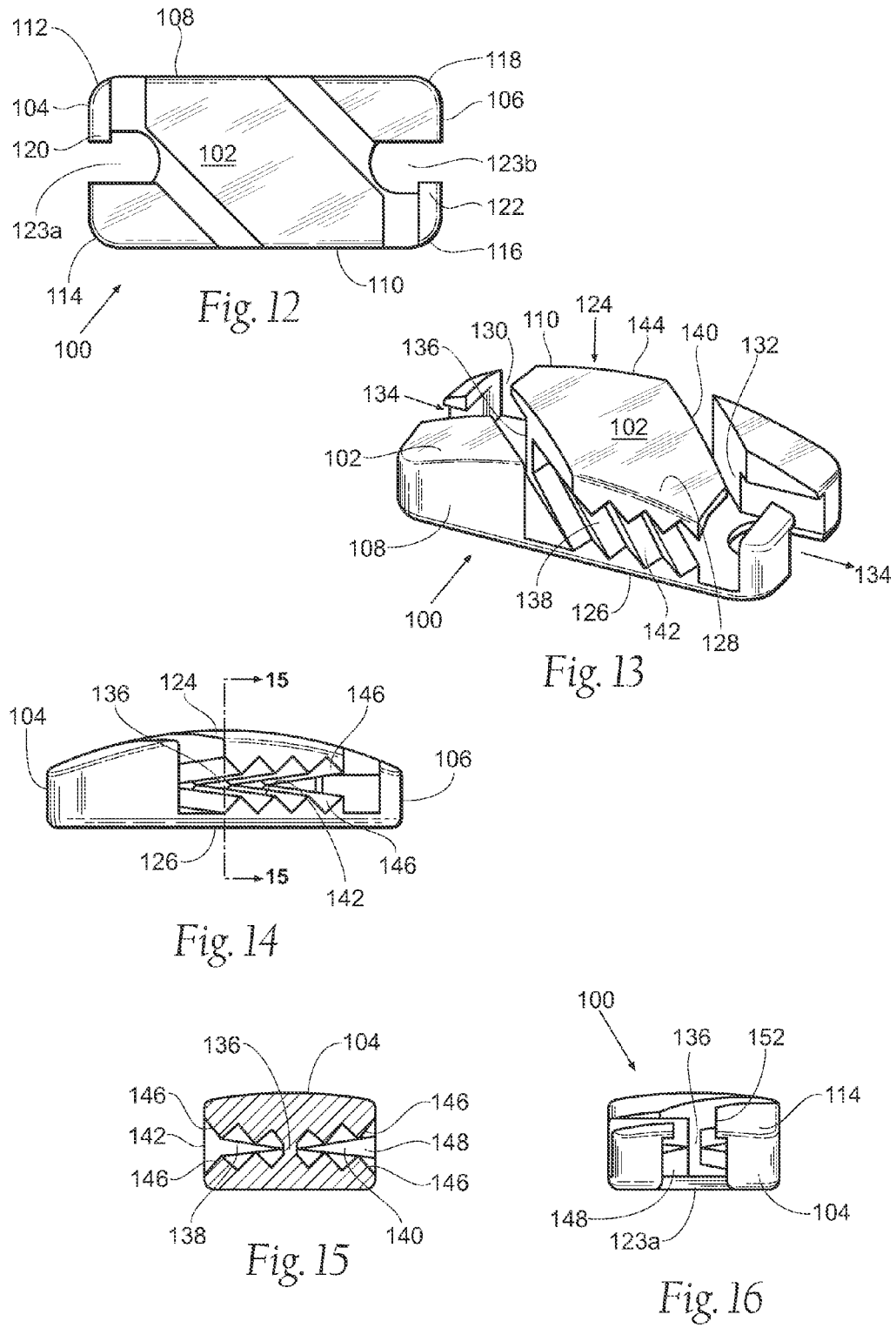

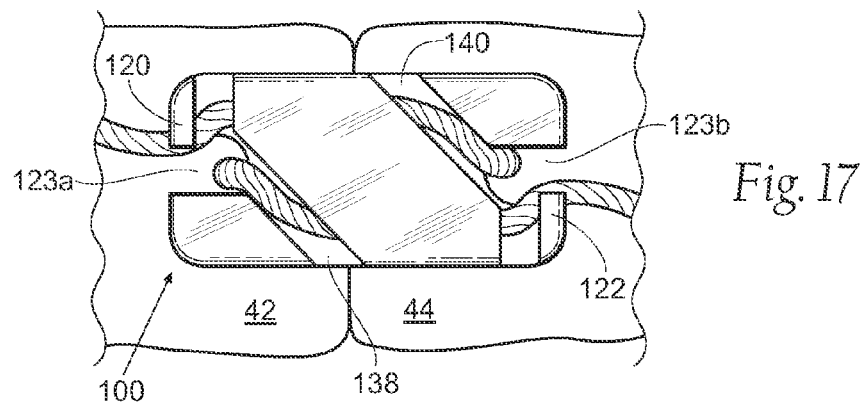
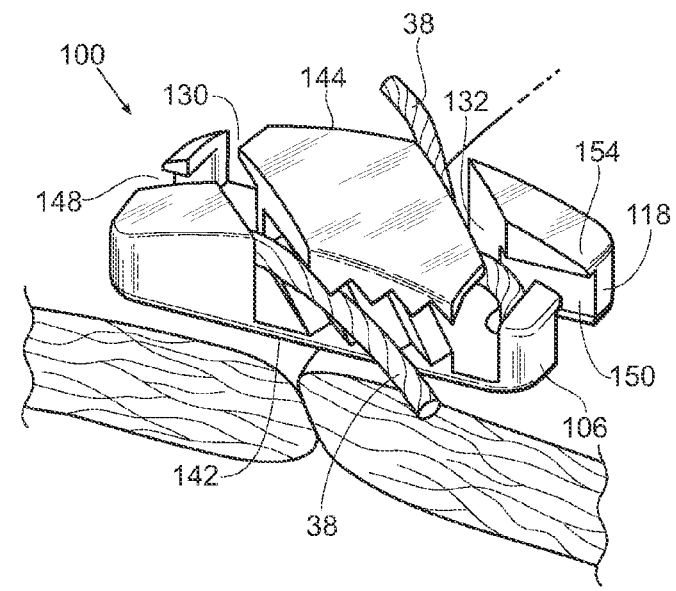
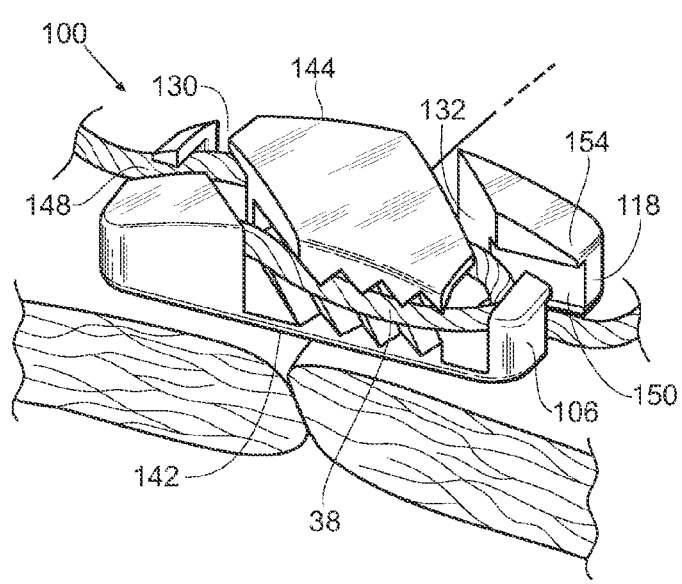

SUTURE LOCK

RELATED APPLICATION

This application is a continuation of U.S. patent application Ser. No. 10/841,255, filed on 7 May 2004, now U.S. Pat. No. 7,862,584, and entitled "Suture Lock," which claims the benefit of U.S. provisional patent application Ser. No. 60/468,496, filed 7 May 2003.

BACKGROUND OF THE INVENTION

The need for this invention arises from surgical practice and procedures, particularly surgical practice and procedures using laparoscopic instruments. Utilizing laparoscopic instruments involves making two or more small incisions in the area of the surgical site. A laparoscopic video camera is inserted into one of the incisions to view the field of the operation inside the patient and laparoscopic surgical instruments are inserted in other incisions and manipulated from outside the patient's body using a video screen visualization, usually enlarged, to guide the work.

Anything that can reduce the number of steps to be performed during surgery can markedly reduce the stress of the procedure, both on the patient and on the doctor. Reducing the number of steps will also reduce the time involved for the procedure, which is a priority in invasive procedures. Surgeons performing such operations are under considerable stress because remote manipulation of the surgical instruments using a video screen for visualization, rather than seeing the site of the operation directly, requires the learning of a great many techniques that are radically different from those performed when the surgical site is open to view. The required techniques include indirect hand-eye coordination and the cooperation between surgeons to place and secure sutures at the surgical site.

The placing of sutures during a laparoscopic surgical procedure may require two surgeons. The surgeons must cooperate in a multi-step process performed with multiple surgical instruments to manipulate the suture needle and the suture. The needle and suture are passed back and forth from one to the other, while placing the sutures and while tying one or more knots.

Finally, sutures have been tightened and secured by tying knots in the sutures. Such knots permanently fix a suture in place and are not able to be removed once in place without removing the entire suture. While some knots have been designed to be tightened further after placement, none allow the surgeon to loosen them if needed to reduce excessive tension on the tissue, which can prevent blood flow to the wound inhibiting healing and producing excessive scare tissue, after the suture is properly tied.

Suture locks and cooperating devices have been developed to simplify the laparoscopic surgical process. For instance, suture locks disclosed in U.S. Pat. Nos. 5,413,585, 5,735,877, 5,741,301, 5,895,393, 6,015,428 and 6,475,229, the specifications of which are incorporated herein by reference, have made the surgical process easier.

Wilk, U.S. Pat. No. 5,391,173, describes a suture device for locking a suture. The device requires that a suture is forced into a small opening or inserted into a larger opening that does not have a retaining mechanism. Colvin et al., U.S. Pat. No. 6,066,160, describes a suture locking device that requires threading of the suture through a small aperture. Schwartz et al., U.S. Pat. No. 6,432,123, describes a suture locking device that uses a locking ring to hold the suture in place. These patents contain advancements over the prior art, but still leave room for improvement, such as the ease of feeding a suture through these devices, the overall time needed to properly tie or knot a suture using these devices, or the ability to easily remove the suture from these devices to reduce suture tension as needed.

SUMMARY OF THE INVENTION

It is an object of the present invention to provide a suture lock that will sufficiently lock a suture in place in a quick and efficient manner. This novel design approach allows a single surgeon working in a laparoscopic environment to suture a surgical site with one or more suture locks and without the need of tying complex or multi-step knots. The suture lock generally comprises a body having an opening that allows a suture to be fed through the body. A plurality of serrated teeth extends into the opening in such a manner that an inserted suture will be locked in place.

It is a further object of this invention to provide a structure lock whereby the suture thread can be easily inserted into the suture lock passageway or passageways.

It is a further object of this invention to provide a suture lock in which the suture thread can be engaged in the suture lock passageway or passageways without passing any end of the suture or needle through an aperture in the structure.

It is a further object of this invention to provide a structure lock in which the suture thread can be easily cinched to close the surgical site.

It is a further object to provide a structure lock that can be easily fabricated.

It is yet a further object to fabricate the structure lock from material or materials that naturally dissolve within the human body.

It is yet a further object of this invention to provide a suture lock that can be easily used by a surgeon at a laparoscopic surgical site with minimal training.

It is another object of this invention to provide a suture lock having a one-way clutching capability whereby the suture thread can be pulled in one direction to cinch the suture thread and close the surgical site while the suture thread resists being pulled in the opposite direction.

It is yet another object of this invention to provide a suture lock whereby increased tension in a first suture end increases the clutching capability on the suture lock on the second suture end.

It is yet another object of this invention to provide a suture lock whereby the suture thread can be released by the surgeon if desired for instance to reduce suture tension, but otherwise remains in its secured and/or cinched state.

BRIEF DESCRIPTION OF THE DRAWINGS

FIG. 1 is a top plan view of a first embodiment of a suture locking device in accordance with the present invention.

FIG. 2 is a sectional view of the device in FIG. 1 taken along the line 2-2 of FIG. 1.

FIG. 3 is a perspective view of the device in FIG. 1.

FIG. 4 is a front elevational view of the device in FIG. 1.

FIG. 5 is a side elevational view of the device in FIG. 1.

FIG. 12 shows a top plan view of a second embodiment of a suture locking device in accordance with the present invention.

FIG. 13 shows a perspective view of the suture locking device in FIG. 12.

FIG. 14 shows a side elevational view of the suture locking device in FIG. 12.

FIG. 15 shows a sectional view taken along the line 15-15 of FIG. 14.

FIG. 16 shows a front elevational view of the suture locking device in FIG. 12.

FIG. 17 shows a top plan view of the suture locking device in FIG. 12 interacting with a suture thread.

FIG. 18 shows a perspective view of a suture thread being fed into the suture locking device of FIG. 12.

FIG. 19 shows a perspective view of the arrangement shown in FIG. 17.

DESCRIPTION OF THE PREFERRED EMBODIMENTS

Figure 6:
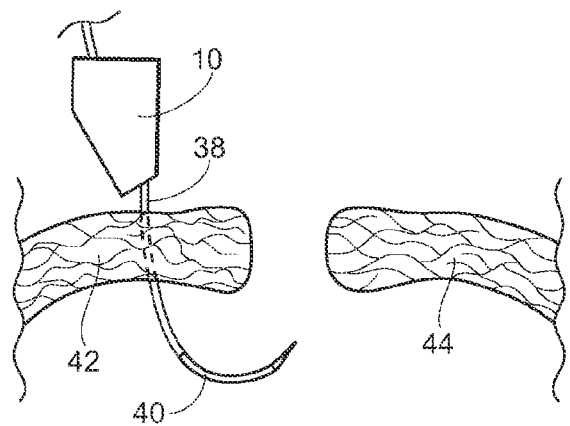
FIG. 6 depicts a suture threaded between two sections of tissue and utilizing the present invention.

Although the disclosure hereof is detailed and exact to enable those skilled in the art to practice the invention, the physical embodiments herein disclosed merely exemplify the invention that may be embodied in other specific structure. While the preferred embodiment has been described, the details may be changed without departing from the invention.

FIG. 1 depicts an overhead view of a suture lock 10 in accordance with the present invention. The suture lock has a main body 12, which provides support when a suture is fed into the suture lock 10. An elongated opening 14 having an open end 16 and a terminal end 18 is located within the body 12. The opening 14 preferably has a curved hook-shaped path, with the open end 16 being larger than terminal end 18. The open end 16 is preferably substantially larger than a suture thread that will be fed into the suture lock 10, thereby easing the process of feeding a suture thread into the suture lock 10, while the terminal end 18 is smaller than a suture thread, thereby providing an area for a suture thread to be secured within the body 12.

Still referring to FIG. 1, a plurality of serrated teeth 20 is located near the terminal end 18 of the opening 14. The serrated teeth 20 are located on opposing sides of the opening 14 and converge towards each other, forming a v-shape arrangement and terminating at a point 22 located at the terminal end 18 of the opening 14. As will be shown and described, the serrated teeth 20 provide locking means for a suture when it is fed into the suture lock 10.

FIG. 2 is a sectional view of the suture lock 10 taken along line 2-2 of FIG. 1. The suture lock 10 has a top side 24 and a bottom side 26. The opening 14 will extend through the height of the body 12 of the suture lock 10, extending from the top side 24 to the bottom side 26. The serrated teeth 18 will also preferably extend through the height of the body 12, as well as the open end 16. The top side 24 has a flat portion 28 and an angled portion 30 and the bottom side 26 is preferably flat. The open end 16 and the terminal end 18 of the elongated opening 14 preferably terminate in the same portion of the top side 24, and preferably terminate within the flat portion 28. The angled portion 30 of the top side 24 assists the user when inserting a suture into the opening 14. The body 12 has a front face 32 and a rear face 34. The front face 32 is angled inwardly from the angled portion 30 of the top side 24 towards the bottom side 26.

FIG. 3 shows a perspective view of the suture lock 10. A through bore 36 is located on the front face 32. The through bore 36 will allow a suture to be inserted into and secured to the suture lock 10. The through bore 36 is sized sufficiently to allow a suture to be slidably inserted into the through bore and preferably sized so that there will be minimal side-to-side movement of a suture within the through bore 36. FIGS. 2 and 3 further show that the serrated teeth 18 are angled downwardly from the top side 24 and tapered toward the rear face 34.

FIG. 4 shows a front elevational view of the suture lock 10. The through bore 36 preferably is located approximately across from the open end 16 of the elongated opening 14 and away from the terminal end 18 of the elongated opening 14. The through bore 36 preferably is positioned at an angle that is substantially perpendicular to the serrated teeth 20. As previously stated, the terminal end 18 is closed and culminates in the point 22. It should be understood that the point 22 covers any arrangement that ends the opening 14, provided that the arrangement is sufficient to secure a suture within the terminal end 18. The position of the through bore 36, as shown in FIG. 4, allows a suture to be fed into the through bore 36 and into the elongated opening 14 without catching on the serrated teeth 20. However, the position is only exemplary, and the through bore 36 may be positioned anywhere on the body 12. The open end 16 is noticeably larger than the terminal end 18, which allows for easy feeding of a suture into the elongated opening 14 (see FIG. 11).

FIG. 5 shows a side elevational view of the suture lock 10. As previously stated, the bottom side 26 is flat or level and the top side 24 has a flat portion 28 and an angled portion 30. The flat sides of the suture lock 10 will allow the suture lock 10 more easily to be held in place and positioned, as opposed to a design having rounded top and bottom sides. However, the shape of the suture lock 10 is merely exemplary of numerous shapes and the suture lock 10 should not be limited to any specific geometric shape or group of geometric shapes.

FIGS. 6-9 show the suture lock 10 being used to close a wound or incision. A suture or suture thread 38 having a needle 40 at its end will be inserted into a first section of tissue 42 and then into a second section of tissue 44. As shown in FIG. 6, the needle 40 is fed into the first section of tissue 42, preferably with the suture 38 and the needle 40 already fed through and attached to the suture lock 10. The suture 38 may be secured within the bore 36, as shown with respect to FIGS. 10-11. Preparing and attaching the suture 38 to the bore 36 in advance will save time in the overall process of cinching together the sections of tissue 42 and 44. The suture lock can be pre-attached to the suture 38 within the bore 36 by the use of many methods including, adhesives, cements, pre-tied knots, thermal fusing, crimping or any combination of more than one of these methods.

Figure 7:
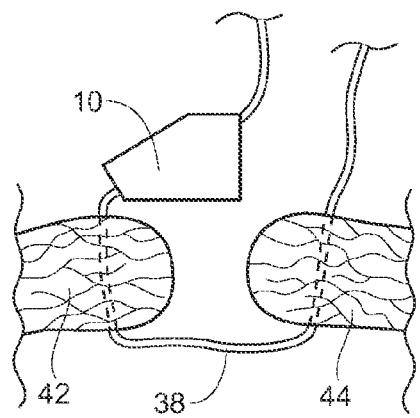
FIGS. 7-9 further depict the suture of FIG. 6 utilizing the present invention.
Figure 8:
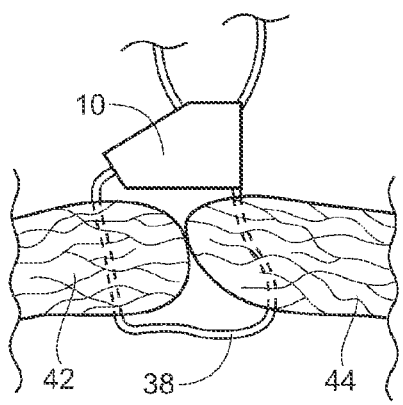
Figure 9:
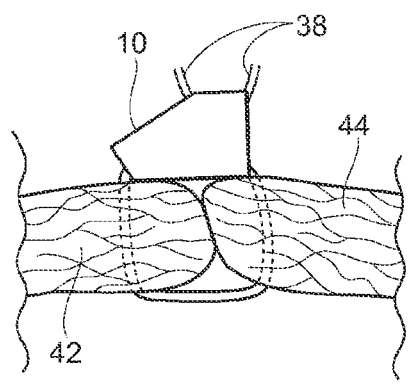

Referring to FIGS. 7 and 8, the suture 38 and the needle 40 now are shown fed through both the first section of tissue 42 and the second section of tissue 44. The sections 42 and 44 are drawn close together, as shown in FIG. 8, and the suture 38 is fed back into the elongated opening 14. When the suture 38 is drawn through the tissue with sufficient tension, the suture 38 will be fed into the terminal end 18 of the elongated opening 14 and cinched within the serrated teeth 20 (FIG. 9), thereby sufficiently closing the gap between the sections of tissue 42 and 44 and securing the sections 42 and 44 in place. Once the suture 38 is secured sufficiently, the excess ends of the suture 38 above the suture lock 10 may be cut away for a cleaner and neater arrangement.

Figure 10:
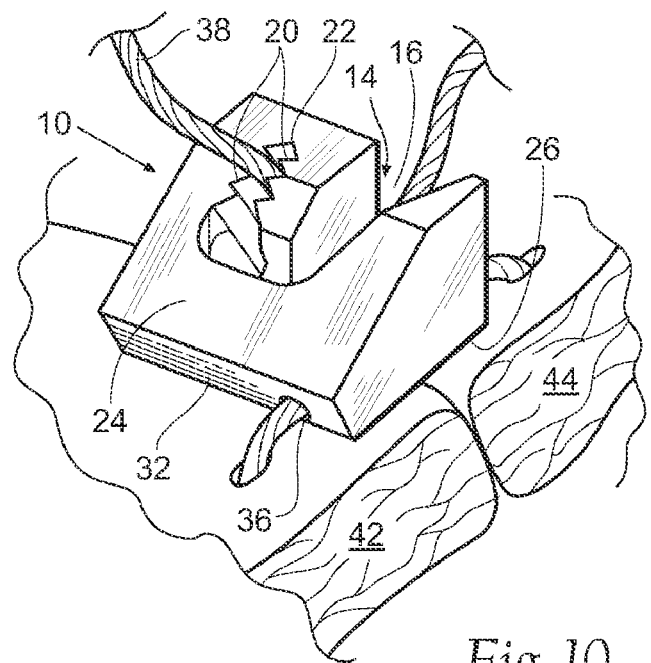
FIG. 10 shows a perspective view of the embodiment of FIG. 1 interacting with a suture thread.

FIG. 10 shows an arrangement of the suture 38 and suture lock 10. The suture 38 is fed through the through bore 36 entering through the open end 16 of the elongated opening 14 and exiting on the front face 32. The suture 38 will enter the first section of tissue 42 and into the second section of tissue 44. The suture 38 then will reenter the suture lock 10 through the open end 16 of the elongated opening 14 on the bottom surface 26. The suture 38 is fed into the serrated teeth 20 in a crosswise path exiting the suture lock 10 on the top side 24. The length of the suture 38 crosses itself within the suture lock 10. The suture 38 can be easily tensioned to approximate or cinch the two sections of tissue 42 and 44 by sliding the suture 38 up through the serrated teeth 20 in the direction of the angled edges of the teeth 20, which direct the suture away from the point 22. The suture 38 cannot slide in the opposite direction down through the teeth 20 as the angled edges draw the suture 38 into the point 22, locking the suture 38 in place. This creates a one-way tensioning clutch. Further, by utilizing the described crosswise path, increasing tension on the end of the suture thread 38 increases tension in the suture 38 as it exits the front 32 of the suture lock 10 from the bore 36, which pulls the suture thread 38 into the suture lock 10. Increased suture tension increases the normal force from the serrated teeth 18 of the suture lock 10 to the longitudinal axis of the suture 38, further locking the suture 38 in place.

Figure 11:
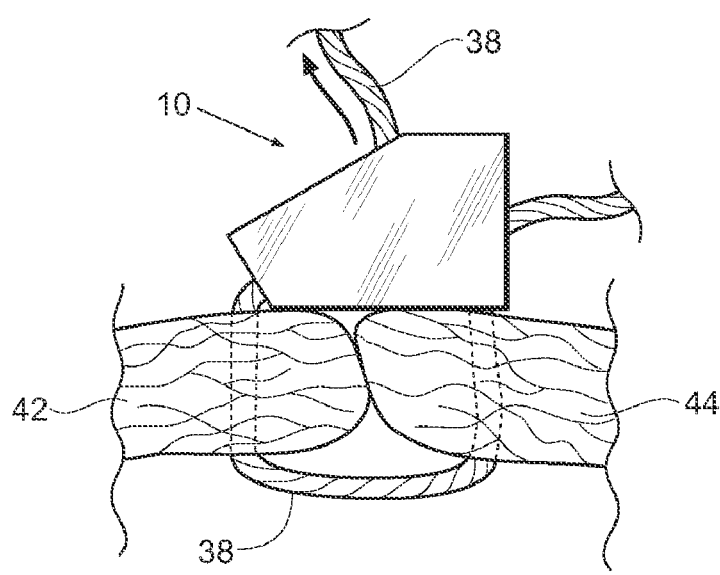
FIG. 11 shows a side elevational view of the arrangement shown in FIG. 10.

FIG. 11 shows a side elevational view of the arrangement in FIG. 10 and demonstrates the crosswise path of the suture. It will be obvious to those skilled in the art that the surgeon can overcome the one-way clutching mechanism of the suture lock 10 by guiding the suture 38 out of the elongated opening 14, reducing the tension and reinserting the suture 38 into the elongated opening 14. Such reinsertion may be necessary, for example, if too much tension has been applied, which could possibly damage the tissue 42 and 44. In this manner, the suture lock 10, although providing secure locking force that increases with increasing tension, is easily reversible once in place without cutting the suture 38 and starting the process from the beginning. FIG. 12 shows an overhead view of a second embodiment of a suture lock 100 according to the present invention. The suture lock 100 has a main body 102 having a front 104, a rear 106, and two sides 108 and 110. The suture lock 100 further has four corners 112, 114, 116, and 118. The corners 112 and 116 have extending tabs 120 and 122, respectively. The tabs 120 and 122, which may help guide the suture 38 when fed through the suture lock 100, will be described in further detail below. An entrance opening 123a, located near the front 104 of the body 102, and an exit opening 123b, located near the rear 106 of the body 102, allow for the suture 38 to be slidably fed in to and out of the suture lock 100 (see FIG. 17). As shown, the suture lock 100 preferably has a generally quadrilateral shape, with the body 102 having a symmetrical design.

FIG. 13 shows a perspective view of the suture lock 100. The body 102 has a top surface 124 and a bottom surface 126. The top surface 124 has a central section 128, and two cutout sections 130 and 132 located near the front 104 and the rear 106 of the body, respectively. The cutout sections 130 and 132 facilitate feeding of the suture 38 through the suture lock 100, as will be described with respect to FIGS. 17-22.

Still referring to FIG. 13, a channel 134 runs longitudinally through the body 102 of the suture lock 100, from the front 104 to the rear 106. A spine 136, extending from the central section 128 of the top surface 124 down to the bottom surface 126, bifurcates the channel 134 into a first passageway 138 and a second passageway 140, located proximate to the central section 128 and preferably parallel to one another. The sides 108 and 110 have longitudinal openings 142 and 144, respectively, also located proximate to the central section 128. The openings 142 and 144 further facilitate feeding of the suture 38 through the suture lock 100, as described with respect to FIGS. 18-19.

FIG. 14 shows a side elevational view of the suture lock 100. A plurality of serrated teeth 146 is shown extending from the spine 136 into the first passageway 138. The serrated teeth 146 are preferably located on the central section 128 along the top surface 124 and also along the bottom surface 126. The opening 142 allows access to the serrated teeth 146 along the first passageway 138. The teeth 146 converge from the rear 106 towards the front 104. It should be noted that serrated teeth 146 are arranged and extend into the second passageway 140 similarly as shown for the first passageway 138 (see FIG. 15), with the exception that in the second passageway 140 the teeth 146 converge in the opposite manner from the front 104 towards the rear 106. FIG. 14 is exemplary for the preferred symmetrical design of the suture lock 100 and should not be considered as limiting the suture lock 100 to any specific orientation. For instance, if the teeth 146 in the passageway 138 would converge from the front 104 to the rear 106 the suture thread could be inserted in an opposite manner and the suture lock would still fall within the scope of the invention.

FIG. 15 is a sectional view of the suture lock 100 taken along the line 15-15 of FIG. 14. As previously stated with respect to FIG. 14, the serrated teeth 146 in passageway 138 converge towards the front 104 of the suture lock 100 and in passageway 140 converge towards the rear 106. The teeth 146 in both passageways also taper inwardly from the openings 142 and 144, converging at the spine 136, preferably centrally of the spine and of the passageways 138 and 140. Essentially, the passageways 138 and 140 taper inwardly from the openings 142 and 144 towards the spine 136.

FIG. 16 shows a front elevational view of the suture lock 100. The front 104 of the suture lock 100 comprises a central portion 148, where the entrance opening 123a is located. The rear 106 of the suture lock 100 has a similar central portion 150, where the exit opening 123b is located (see FIG. 17). The corner 114 has a lip 152, which assists in orientating the suture 38 in place within the suture lock 100 (FIG. 16). A similar lip 154 is located on the corner 118 (see FIG. 18). The front central portion 148 and the rear central portion 150 are sized sufficiently to allow the suture 38 to be inserted easily into and through the suture lock 110.

FIGS. 17-22 show the suture 38 being fed through the suture lock 100. FIG. 17 shows an overhead view of the suture lock 100 cinching together the sections of tissue 42 and 44. The suture 38 will proceed from the first section of tissue 42, through the entrance opening 123a and along the first passageway 138, passing underneath the tab 122 and exiting the suture lock 100. The suture 38 also passes between the first tissue section 42 and the second tissue section 44 (see FIG. 20) and enters the suture lock 110 at the exit opening 123b (see FIG. 17). The suture 38 further proceeds along the second passageway 140 and exits the suture lock 100 underneath the tab 120.

FIG. 18 shows a perspective view of the suture lock 100. The suture 38 is shown extending outwards of the openings 142 and 144. The openings 142 and 144, along with the cutout portions 130 and 132, assist in adjusting and orientating the suture 38 by providing substantial space for the suture 38 to be slid within the suture lock 100. The open areas allow the suture 38 more easily to be adjusted than in other suture lock designs that may require a suture to be fed through a closed hole or tunnel. One skilled in the art will also appreciate that the openings 142 and 144 may be situated in the central section 128 of the body and provide the same easy feeding process as described herein.

FIG. 19 shows a perspective view of the suture lock 100 securing the suture 38. The suture 38 will be pulled outwardly through the central portions 148 and 150 through the serrated teeth 146. The angles of the teeth 146 allow the suture 38 to be retained within the teeth 146 as it is pulled through the suture lock 100, without the suture 38 retracting in the opposite direction.

Figure 20:
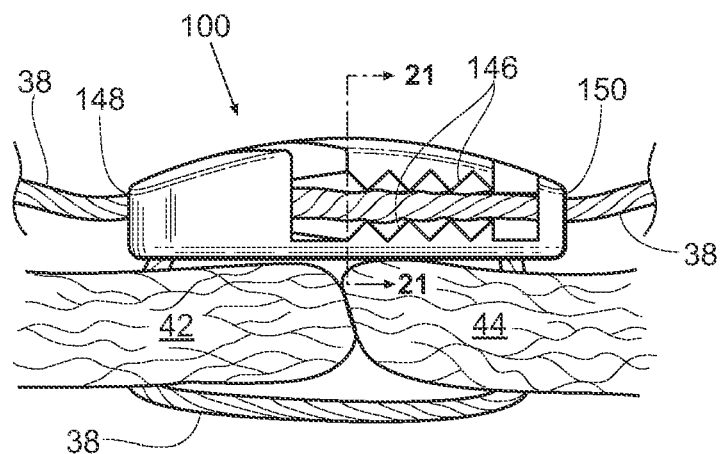
FIG. 20 shows a side elevational view of the arrangement shown in FIG. 17.

FIG. 20 shows a side elevational view of the suture lock 100. The suture 38 will be pulled outwardly through the central portions 148 and 150. The opposing angles of the serrated teeth 146 allow the suture 38 to be pulled outwardly with minimum tension. Because the central portions 148 and 150 are preferably longitudinally axially aligned with the spine 136, pulling outwardly through the central portions 148 and 150 will cause the suture 38 to move inwardly onto the teeth 146, thereby securing the suture 38 within the suture lock 100. The angles of the serrated teeth 146 inhibit the suture 38 from being pulled inwardly through the central portions 148 and 150. These angles further move the suture 38 inwardly onto the teeth 146, increasing the locking force.

As was previously described herein, the two passageways 138 and 140 are preferably substantially parallel. Because they are parallel and offset from the center longitudinal axis where the suture thread 38 enters and exits the device creates essentially a "C" shaped path. The tensile force on one end of the suture 38 creates a normal force between the suture 38 and the suture lock 100 (see FIG. 17). The "C" shape when tensioned will tend straighten out. The normal straightening force is transferred to the other end of the suture 38 and increases the locking force of the device. In a similar manner to the cross wise path of the suture 38 in the first embodiment 10 shown herein (see FIGS. 10-11), the offset parallel path of the suture 38 in this second embodiment increases the suture locking forces of the device and thereby reduces the possibility of the suture thread 38 detaching from the suture lock 100.

Figure 21:
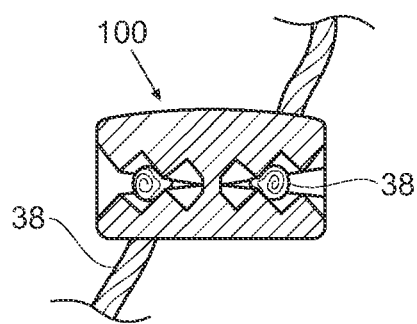
FIG. 21 shows a sectional view of the arrangement shown in FIG. 20 taken along the line 21-21.

FIG. 21 shows a sectional view of the suture lock 100 and the suture 38 taken along the line 21-21 of FIG. 20. As described with respect to FIG. 20, the suture 38 is shown interacting with the teeth 146. The suture 38 is pinched within the teeth 146, and the suture lock 100 will firmly hold the suture 38 and the tissue sections 42 and 44 in place (see FIG. 20).

Figure 22:
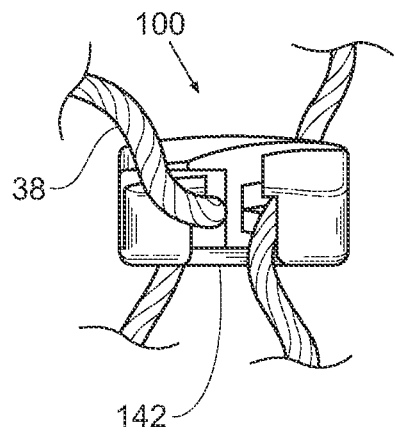
FIG. 22 shows a front elevational view of the arrangement shown in FIG. 17.

FIG. 22 shows a front elevational view of the suture lock 100 interacting with the suture 38. As previously stated, the front central portion 148 (and also the rear central portion 150) are sized sufficiently to allow two sections of the suture 38 to slidably pass through the central portion 148 (and 150) in a manner that will generally prevent binding of the suture 38 when outward tensioning is applied to produce additional tissue approximation.

The present invention, especially with reference to the embodiments 10 and 100, is advantageous over prior art arrangements in that the suture 38 does not need to be fed through an aperture within the suture lock. Because of the open-ended passageways and openings in the present invention, a surgeon has more leeway when feeding a suture thread into the suture lock, thereby quickening and reducing the stress associated with the feeding process. The suture 38 may be unobstructedly placed within the opening, which reduces time and stress for the surgeon.

The present invention also helps to reduce tension across the suture 38 and the sections of tissue 42 and 44. The arrangement of the plurality of angled serrated teeth allows the suture lock to spread the tension of the suture over the entire length of the suture, as opposed to the specific cinching areas of the suture. That is, the suture lock will provide a predetermined tension that is substantially evenly distributed through segments of the suture adjacent and in the suture lock.

Likewise, the present invention allows the suture thread to be fed through separate and distinct holes within the tissue. As opposed to knotting of a suture within the tissue, the suture lock spreads tension that may cut, tear, or elongate the tissue horizontally across the tissue, preventing possible tissue damage. The suture lock also provides a device where the vector or direction of the tension is parallel to the adjoining area of the two pieces of tissue. This is advantageous over knots and prior art arrangements in that the suture is not preloaded, which may tear the tissue in the direction of the wound. The suture lock bridges an interface of sections of sutured tissue substantially parallel to the tissue interface, reducing overall stress on the tissue.

Figure 23:
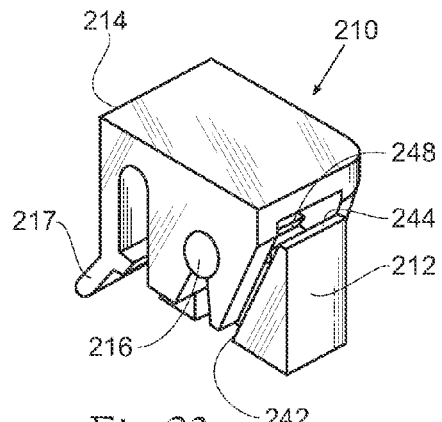
FIG. 23 shows a perspective view of a further embodiment in accordance with the present invention.

Referring to FIG. 23, a perspective view of a third embodiment 210 of a suture lock according to the present invention is disclosed. The suture lock 210 is generally comprised of a first sliding section 212 and a second base section 214. The sections 212 and 214 are slidable with respect to one another. The suture lock 210 further has guide means 216 located between the sliding section 212 and the base section 214, which assists the sections 212 and 214 when moving with respect to one another. The suture lock 210 preferably comprises a generally cubical or parallelepiped shape. Release means, shown as a tab 217, or another structure may be situated on the suture lock 210 to assist in orientating the suture 38 and the suture lock 210, but the suture lock 210 is basically of a box-like structure.

Figure 24:
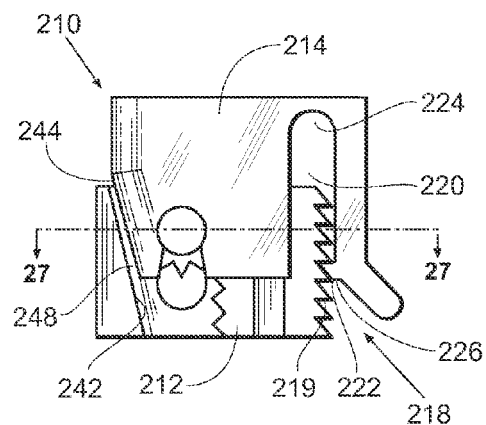
FIG. 24 shows an elevational side view of the embodiment shown in FIG. 23.

FIG. 24 shows a side elevational view of the suture lock 210. The suture lock 210 further comprises retention means 218 for holding together the first section 212 and the second section 214 in a relative position with respect to one another. The retention means comprises a toothed edge 219 located on the sliding section 212. The toothed edge 219 is inserted into an elongated opening 220 located in the base section 214, with the elongated opening 220 having an open end 222 and a terminal end 224. The retention means 218 further comprises a pawl 226 located at the open end 222 of the elongated opening 220. The pawl 226 interacts with the toothed edge 219 located on the sliding section 212 to adjust the position of the sections 212 and 214, thereby securing the suture 38 (see FIGS. 31 and 32). The terminal end 224 is shown as being rounded, which will allow the elongated opening 220 to flex sufficiently so that the pawl 226 may continue to move along the toothed edge 219, when necessary. The retention means 218 as shown and described are merely exemplary of possible retention means. Provided that a retention device or assembly will allow the sections 212 and 214 to be retained in a specific position with respect to one another, the device would fall within the scope of the invention.

Figure 25:
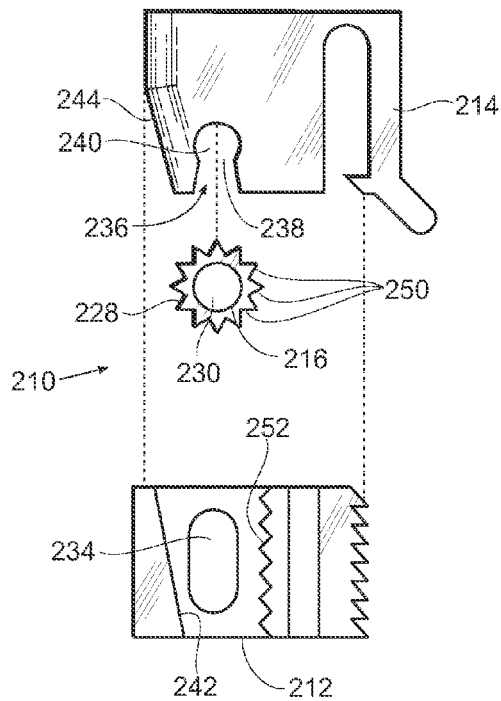
FIG. 25 shows an exploded side view of the embodiment shown in FIG. 23.
Figure 26:
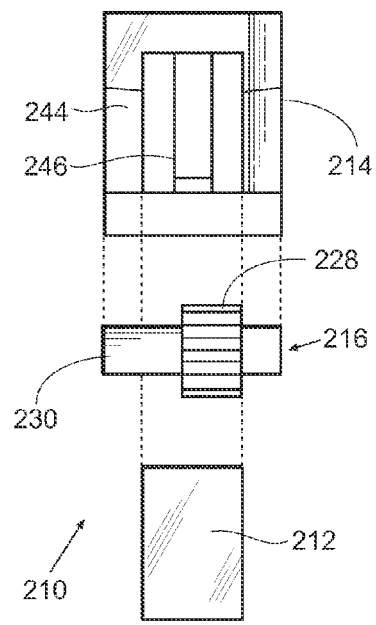
FIG. 26 shows another exploded front view of the embodiment shown in FIG. 23.

FIGS. 25 and 26 show exploded views of the suture lock 210. The guide means 216, as shown, comprises a gear 228 located on a shaft 230. The gear 228 will interact with a toothed or serrated section 250 located on the sliding section 212. A slot 234, located on the sliding section 212, and a second opening 236, located on the base section 214, allow the shaft 230 to be rotatably secured to the sections 212 and 214. The second opening 236 has an open keyhole shape, having an entrance 238 and a curved head section 240. The shaft 230 is fittingly snapped within the curved head section 240, thereby rotatably retaining the shaft 230 within the base section 214. The slot 234 further allows the sliding section 212 to slide relative to the suture lock 210 without being constrained by the shaft 230.

Still referring to FIGS. 25 and 26, the sliding section 212 is shown having an angled surface 242. The angled surface 242 will correspond to a tapered side 244 located on the base section 214. The arrangement of the angle surface 242 and the tapered side 244 help the sliding section 212 and the base section 214 to slide relative to each other. The sliding section 212 is sized to fit within a cavity 246 located within the base section 214. Before the sliding section 212 is inserted into the cavity 246, the shaft 230 of the guide means 216 will be inserted within the slot 234, and the sliding section 212 and the guide means 216 will be inserted into the base section 214 together as an assembly.

Referring further to FIG. 25, the guide means 216 comprises the gear 228 located on the shaft 230. The gear 228 has a plurality of teeth 250 that interact with a toothed section 252 located on the first section 212. Preferably, the shaft 230 is rotatably secured to the first section 212, and the gear is in a sliding relationship with the toothed section 252 located on the second section 214. As the shaft 230 rotates, the teeth 250 will move along the serrated section 252 and keep the sections 212 and 214 relatively aligned with one another. Essentially, the guide means, as shown, comprises a rack and pinion arrangement. The toothed section 252 comprises the rack and the gear 228 comprises the pinion. The teeth 250 on the gear 228 also serve the additional purpose of further locking the suture 38 within the channel 248 (see FIG. 33). As the gear 228 moves along the toothed section 252, the teeth 250 will rotate and catch the suture 38 as it passes through the channel 248. The arrangement provides for further means for the suture to be held in place.

The guide means 216 shown in FIGS. 25 and 26 are merely exemplary of possible drive mean arrangements that may be used within the suture lock 210 and should not be considered as limiting on the scope of the invention. For instance, the guide means may be integrated with one of the sections of the suture lock 210. Likewise, the guide means 216 may comprise a bearing-style arrangement, having a smooth shaft running along a flat surface. The guide means should be considered broadly as any means that assists the sliding section 212 in moving with respect to the base section 214.

Figure 27:
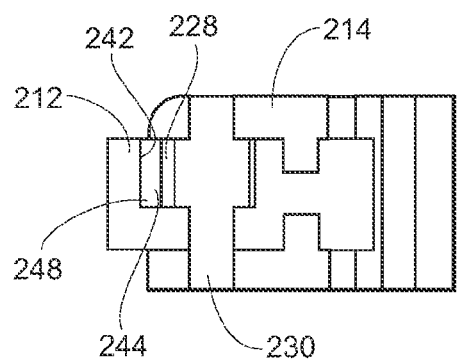
FIG. 27 shows a sectional view of the embodiment shown in FIG. 23 taken along the line 27-27 of FIG. 24.
Figure 28:
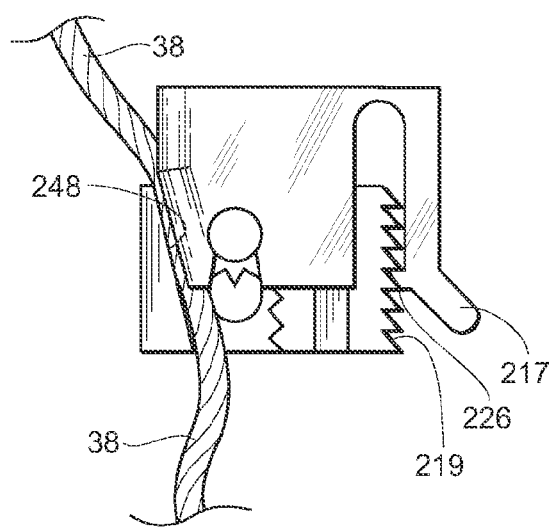
FIG. 28 shows a side elevational view of the embodiment shown in FIG. 23 interacting with a suture thread.

Referring to FIGS. 23, 24 and 27, the angled surface 242 and the tapered side 244 are positioned to form a channel 248 between the sections 212 and 214. As seen in FIG. 28, the channel 248 is in an open position, thereby providing an area for the suture 38 to be inserted into the suture lock 210 (see FIGS. 28-32). As the first section 212 and the second section 214 are slid towards each other, the angled surface 242 moves inwardly towards the gear 228 and the tapered side 244, the channel 248 will move into a closed position (see FIGS. 32 and 33). Because of the retention means 218, the channel 248 may be positioned and retained in numerous positions between an open position and a closed position.

Referring now to FIGS. 28-32, the suture lock 210 is shown interacting with the suture 38.

Figure 29:
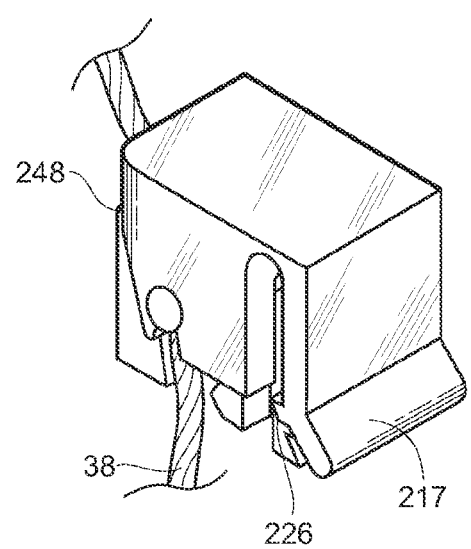
FIG. 29 shows a perspective view of the arrangement shown in FIG. 28.

FIG. 28 shows a side elevational view and FIG. 29 shows a perspective view of the suture lock 210 in a non-locking arrangement with the suture 38. The pawl 226 is shown interacting with the first few teeth of the toothed edge 219. There is still sufficient area left within the channel 248 so that the suture 38 or sutures 38 will be able to slide and tension may be applied to the suture 38 to bring together sections of tissue (not shown).

Figure 30:
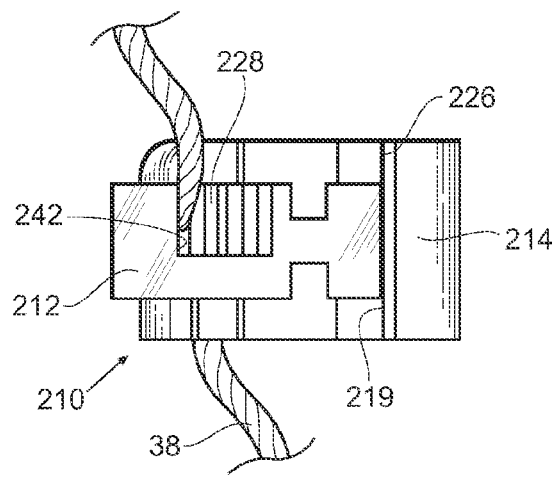
FIG. 30 shows a bottom view of the suture lock depicted in FIG. 23 securing a suture thread.
Figure 31:
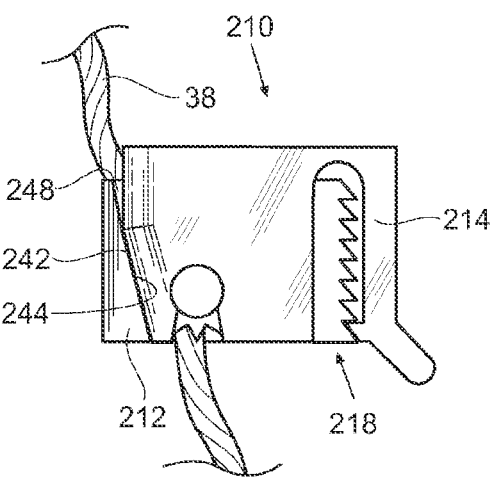
FIG. 31 shows a side elevational view of the arrangement of FIG. 30.
Figure 32:
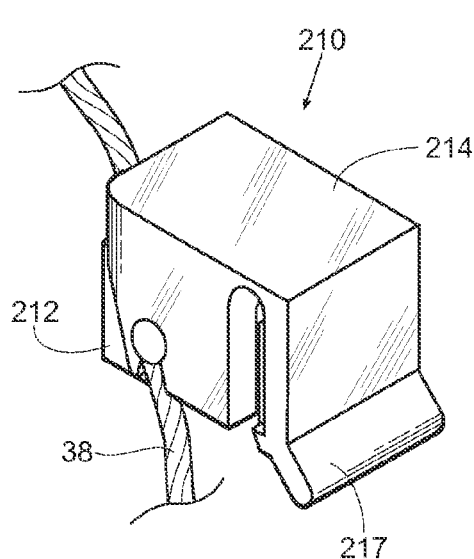
FIG. 32 shows a perspective view of the arrangement of FIG. 30.

FIGS. 30-32 depict views of the suture lock 210 securing the suture 38 in place. FIG. 31 shows a bottom view of the suture lock 210. The pawl 226 is relatively flush with the last tooth of the toothed edge 219. The sutures 38 will be secured in place between the angled surface 242 and the gear 228. As previously stated, the sliding section 212 sits within the base section 214. The suture 38 is secured within the channel 248, with the teeth of the gear 228, catching the suture 38 and holding it in place. Because the retention means 218 do not allow for the sections 212 and 214 to be separated, the teeth of the gear 228 prevent the suture from being retracted through the channel 248.

FIG. 31 shows a side elevational view of the suture lock 210 securing the suture 38 in place. When the suture 38 had been secured, the surfaces of the sliding section 212 and the base section 214 will be preferably flush with one another. The channel 248 is closed, and the suture 38 is retained within the channel 248. FIG. 32 shows a perspective view of the suture lock 210 locking the suture 38 in place. As also shown in FIG. 30, the surfaces of the sliding section 212 and the base section 214 are shown flush with each other. It will be understood that the arrangement described will provide approximation and cinching of tissue, as shown and described with respect to the previous embodiments.

Figure 33:
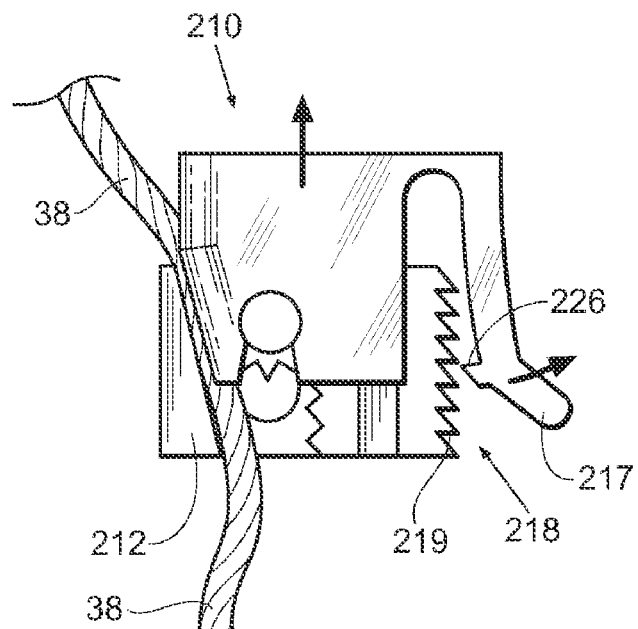
FIG. 33 shows a side elevational view of the embodiment of FIG. 23 utilizing retention release means.

Referring to FIG. 33, once the suture or sutures 38 are secured in place, it may be realized that the proper tension has not been place upon the joined sections of tissue (not shown). Additional tension can be placed on the suture 38. As the suture 38 passes across the gear 228, the suture 38 will rotate the gear 228, which in turn translates the movement to the sliding section 212, and moves the angled surface 242 away from the suture 38, allowing low resistance movement. When the desired tension is achieved, releasing the suture 38 will cause the suture 38 to translate in the opposite direction, which in turn rotates the gear 228 the opposite direction. This translates the sliding section 212 toward the base 214, bringing the angled surface 242 towards the suture locking it again against the gear 228. In this manner, applying and/or releasing tension on the end of the suture 38 may then easily adjust the tension and positioning of the suture 38. Optionally, the release means 217 may then be moved outwardly from the suture lock 210, thereby releasing the retention means 218. The pawl 226 is removed from the toothed edge 219, and the sliding section 212 and the base section 214 may be moved apart from one another. The tension and positioning of the suture 38 may then be adjusted and repositioned, and the suture lock 210 may then be used to resecure the suture 38.

Figure 34:
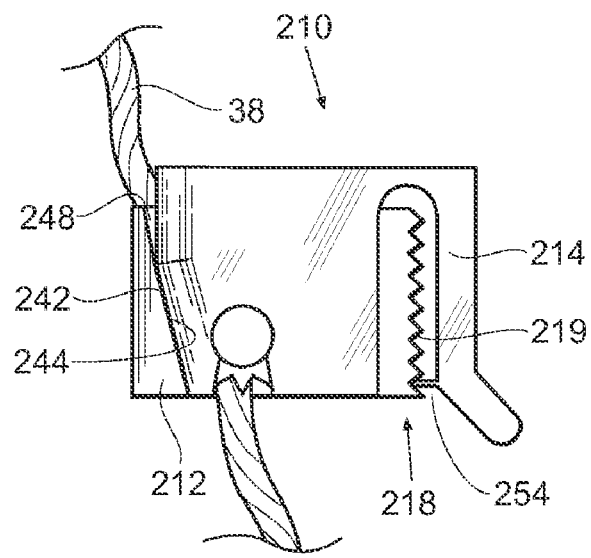
FIG. 34 shows a further side elevational view of the embodiment of FIG. 23 utilizing further retention release means.

FIG. 34 shows a different arrangement of the suture lock, as described with respect to FIG. 33. An indexer 254 has now replaced the pawl 226. The indexer 254 will interact with the toothed section 219 to retain the first section 212 and the second section 214 relative to one another. The indexer 254 is flexible enough so that if the sections 212 and 214 are moved apart by an external force applied by the user, the indexer 254 will allow the toothed section 219 to pass by the indexer 254. The resistance of the indexer 254 could have a wide range of tensions.

The suture lock 210 was described as securing a single suture 38. It will obvious to those skilled in the art that the suture lock 210 may be used to secure multiple sutures 38 if necessary. Likewise the dimensions of the suture lock 210 may be adjusted accordingly for a different number of sutures and still fall within the scope of the invention.

The described suture locks provide a convenient and efficient locking device. Because the teeth are designed to allow a suture generally to be slid in one direction, a minimal force is required to provide tension for a suture. However, the teeth provide adequate resistance so that the suture will not retract in the opposite direction, and the tissue sections will remain secured together. The suture locks are preferably manufactured from a material that will naturally dissolve within the body. Because the suture lock efficiently locks and secures a suture in place, a single surgeon, as opposed to the possibility of requiring two surgeons, may potentially accomplish the suturing process.

The foregoing is considered as illustrative only of the principles of the invention. Furthermore, since numerous modifications and changes will readily occur to those skilled in the art, it is not desired to limit the invention to the exact construction and operation shown and described.

We claim:

1. A one-piece suture lock to be used with a suture thread, said suture lock comprising:
a body comprising:
   a substantially planar left face;
   a substantially planar rear face situated substantially orthogonally to said left face;
   a substantially planar right face situated substantially orthogonally to said rear face and substantially parallel to said left face;
   a first substantially planar top face extending substantially orthogonally from said rear face, and spanning a body length from said left face to said right face;
   a first substantially planar bottom face extending substantially orthogonally from said rear face, substantially parallel to, and spaced a body thickness from, said first top face, and spanning said body length from said left face to said right face;
   a second substantially planar top face extending obliquely from said first top face towards said first bottom face and spanning said body length from said left face to said right face;
   a second substantially planar bottom face extending obliquely from said first bottom face towards said first top face and spanning said body length from said left face to said right face;
wherein said second top face and said second bottom face intersect at a front edge that extends substantially parallel to said rear face and extends from said left face to said right face;
an elongated opening formed in said body, through said body thickness and through said rear face, said first top face, said first bottom face, said second top face and said second bottom face, said elongated opening having an open end formed in said rear face and a terminal end extending through said body thickness and disposed between said open end and said left face; and
a plurality of converging teeth located closer to said terminal end of said opening than to said open end.

* * * * *